United States Patent [19]

Wiseman et al.

[11] Patent Number: 4,598,596

[45] Date of Patent: * Jul. 8, 1986

[54] SAMPLE HANDLING METHOD AND APPARATUS

[75] Inventors: Alan G. Wiseman, Glen Waverley; John T. Huberts, Mount Waverley, both of Australia

[73] Assignee: Varian Techtron Proprietary Limited, Mulgrave, Australia

[*] Notice: The portion of the term of this patent subsequent to May 21, 2002 has been disclaimed.

[21] Appl. No.: 709,250

[22] Filed: Mar. 7, 1985

Related U.S. Application Data

[62] Division of Ser. No. 405,445, Aug. 5, 1982, Pat. No. 4,517,850.

[30] Foreign Application Priority Data

Aug. 5, 1981 [AU] Australia ............................... PF0064

[51] Int. Cl.[4] ........................ G01N 1/14; G01N 35/06; B01L 3/02
[52] U.S. Cl. ............................. 73/864.22; 73/864.01; 73/864.16; 73/864.25
[58] Field of Search ..................... 356/312; 422/100; 73/864.01, 864.02, 864.11, 864.12, 864.13, 864.15, 864.16, 864.17, 864.18, 864.21, 864.22, 864.24, 864.25

[56] References Cited

U.S. PATENT DOCUMENTS

| 4,042,338 | 8/1977 | Huber | 356/312 |
| 4,068,529 | 1/1978 | Konig | 73/864.24 |
| 4,235,840 | 11/1980 | Mendoza et al. | 422/100 |

Primary Examiner—Stewart J. Levy
Assistant Examiner—Tom Noland
Attorney, Agent, or Firm—Stanley Z. Cole; Edward H. Berkowitz

[57] ABSTRACT

A method relating to deposition of a liquid sample mixture in the tubular furnace of a spectrophotometer. The method involves drawing a quantity of each ingredient of the sample mixture into a conduit in a predetermined sequence and also drawing a slug of air into the conduit immediately following the uptake of each ingredient. In the result, a segmented fluid stream is created in which a slug of air separates each two adjacent ingredient segments. The conduit is initially filled with a rinsing fluid and the segmented fluid stream displaces some of that rinsing fluid from the conduit. A slug of air separates the rinsing fluid from the segmented stream. The segmented stream is then discharged in a single operation into the furnace of the spectrophotometer so that mixing of the ingredients occurs at or adjacent the furnace surface. Apparatus for carrying out the method comprises a syringe connected to a nozzle through a conduit, a source of rinsing fluid connected into the conduit at a location between the nozzle and syringe, and means for moving the nozzle across a plurality of ingredient pick-up stations, a rinse station and a deposition station at which the furnace is located.

9 Claims, 4 Drawing Figures

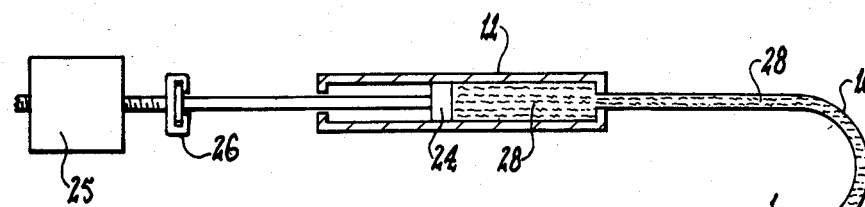
Fig 1
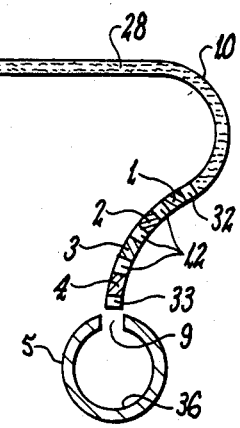
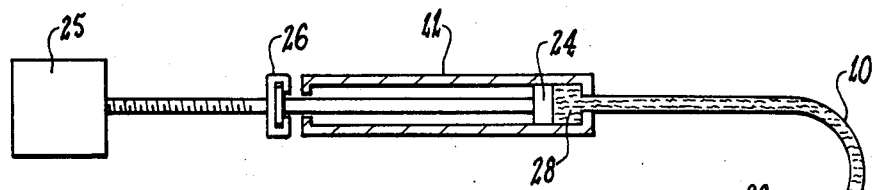
Fig 2
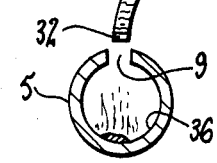
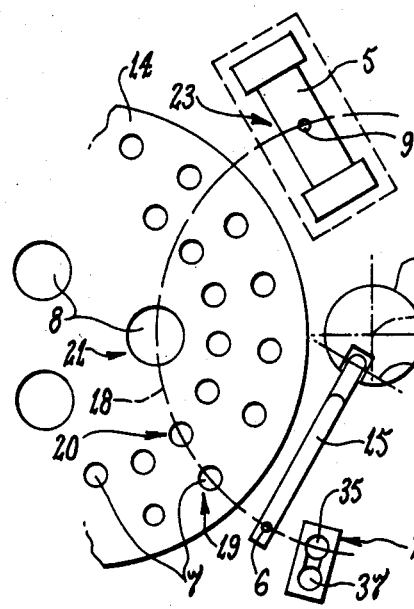
Fig 4

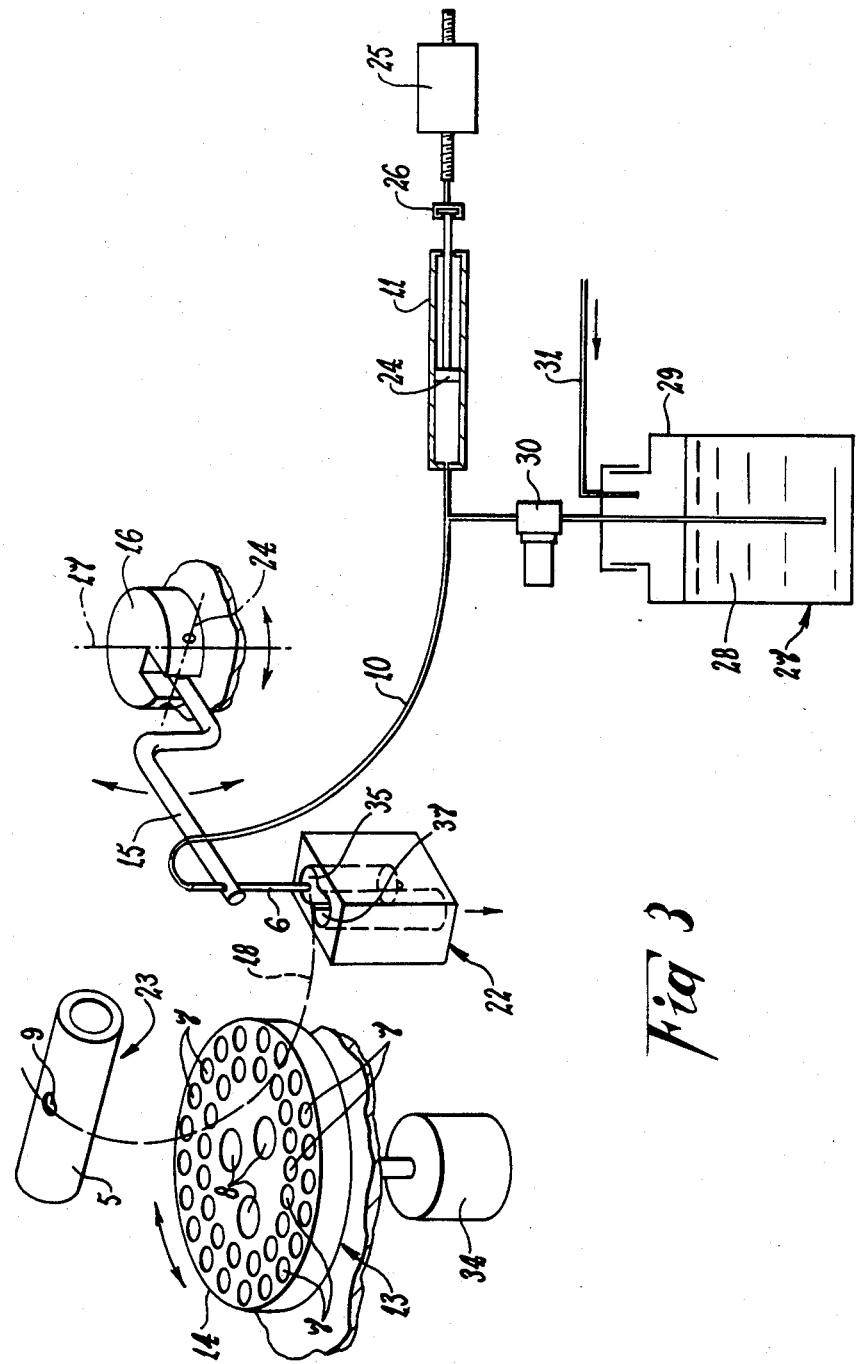

SAMPLE HANDLING METHOD AND APPARATUS

This application is a division, of application Ser. No. 405,445, filed Aug. 5, 1982, and now U.S. Pat. No. 4,517,850.

This invention relates to a method and apparatus for handling samples to be subjected to chemical analysis by spectroscopy of other means. It will be convenient to hereinafter describe the invention with particular reference to spectroscopic analysis in which the sample is analysed in a graphite tube furnace.

It is sometimes necessary in chemical analysis to atomise the sample together with one or more additives. For example, the additive may be a matrix modifier, a standard, or a blank, and two or more of those additives may be used at any one time. The sample and additive or additives may be premixed before introduction to the furnace but that is not entirely satisfactory because of the time involvement and also the difficulty of achieving accuracy in the respective volumes of the constituents. Accuracy is extremely important because of its influence on the results of the analysis and also for the purpose of reproducability of a particular mixture. In an alternative procedure, the ingredients of the mixture are introduced separately into the furnace, but that is also time consuming because of the need to pick-up and introduce each ingredient individually.

A principle object of the present invention is to provide a method and apparatus for simplifying accurate deposition of two or more ingredients of a sample mixture for the purpose of chemical anlaysis. It is a further object of the invention to provide an improved method and apparatus for depositing material to be analysed in a tubular furnace of a spectrophotometer.

According to one aspect of the present invention, there is provided a sample handling method including the steps of, loading into a conduit in sequence a quantity of one ingredient of a sample mixture, a slug of separating fluid and a quantity of another ingredient of said mixture, and depositing said ingredients in succession at a deposition zone in a single operation.

According to another aspect of the invention, there is provided sample handling apparatus including, a conduit, a nozzle at one end of said conduit, sources of positive and negative pressure connectable to said conduit at a location remote from said nozzle, a plurality of pick-up stations at which respective components of a segmented fluid stream to be carried by said conduit are located, and support means carrying said nozzle and being movable to locate said nozzle in a selected sequence at each of said stations and subsequently at a deposition zone.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

In the drawings:

FIG. 1 is a diagrammatic view of the method of conducting the various ingredients of a sample mixture to the deposition zone;

FIG. 2 is a view similar to FIG. 1, but showing the ingredients deposited at the deposition zone;

FIG. 3 is a diagrammatic perspective view of one form of apparatus suitable for carrying out the method of the invention;

FIG. 4 is a plan view of part of the apparatus shown in FIG. 3.

As shown diagrammatically in FIGS. 1 and 2, the method of the invention is characterised in that the various ingredients 1, 2, 3 and 4 of the mixture to be analysed are conveyed simultaneously but in a separated state, to the deposition zone—e.g., tubular furnace 5. The ingredients 1, 2, 3 and 4 are then deposited at that zone in a single operation although they arrive at the zone in a sequential fashion, such that mixing of the ingredients 1, 2, 3 and 4 does not occur before they are close to or settle on the deposition zone. The number of ingredients may vary from four as shown. As previously stated, it will be convenient to describe the invention with particular reference to a spectrophotometer including a graphite tube furnace 5.

Apparatus to which the invention can be applied is shown diagrammatically in FIG. 3 and typically includes a suction operated pick-up device 6 which can be sequentially introduced into a plurality of containers 7 and 8 each of which includes a particular ingredient of the mixture to be analysed. The pick-up device as shown includes a tubular nozzle 6 which is insertable into the containers 7 and 8 and an access opening 9 of the tubular furnace 5, and that nozzle 6 is connected by a capilliary tube 10 or conduit to a source 11 of negative and positve pressure. The various ingredients are therefore drawn into the nozzle 6 and possibly the capilliary tube 10 so as to be arranged therein in series as shown in FIG. 1. According to the present invention however, a slug of air 12 (FIG. 1) or other separating fluid is drawn into the nozzle 6 immediately following the up-take of each ingredient with the result that each two adjacent ingredients in the series are separated one from the other.

The apparatus as shown includes a multi-sample carrier 13 of the kind having a turntable 14 adapted to support a number of sample vials 7. In the example shown, turntable 14 is able to support two groups of vials 7 each of which is arranged in a circle co-axial with the rotational axis of the turntable 14. Each vial 7 within each of the two groups may hold a respective sample solution. The turntable 14 also has means for retaining beakers 8 which may contain respective additives such as a blank solution, matrix modifier and standard solution, and those beakers 8 are conveniently located within the innermost group of vials 7.

In the particular arrangement shown, the pick-up nozzle 6 is supported by an arm 15 which is located to one side of the turntable 14 and is connected to a pivotal mounting 16. The mounting 16 is pivotable about axis 17 so as to move the nozzle 6 along an arcuate path 18 which passes across a plurality of stations. For example, as shown in FIG. 4, there may be three possible pick-up stations 19, 20 and 21 corresponding to vial 7 and beaker 8 locations on the turntable 14, a rinse station 22 to one side of the turntable 14 and a deposition station 23 which includes the tubular furnace 5. The support arm 15 is also arranged for up and down movement about a transverse pivot 24 so that the nozzle 6 might be moved into and out of a vial 7, beaker 8 or opening at each station. A pivotal mounting is not essential for that purpose however, as linear up and down movement would be satisfactory.

Movement of the turntable 14 and nozzle support arm 15 may be controlled through electronic means, perhaps including a micro-processor. That same electronic means may control the source 11 of pressure to which the pick-up nozzle 6 is connected.

The source 11 of negative and positive pressure is preferably a syringe 11 and that may be of the kind forming the subject of Australian Patent Application No. 71369/81. That is, the syringe plunger 24 is driven by a linear drive stepper motor 25 through a direct coupling 26 such that the syringe 11 responds to actuation of the motor 25 in an immediate and accurately predictable manner. Furthermore, the motor actuation is precisely controllable for accurate syringe response.

A source 27 of rinse solution 28 such as distilled water may be connected to the capilliary tube 10 at a location between the syringe 11 and the pick-up nozzle 6 as shown in FIG. 3. In the example shown, the source 27 includes a container 29 for the solution 28 which is connected to the capilliary tube 10 by way of a solenoid or other controllable valve 30. The interior of the container 29 may be pressurised through line 31 by means of an inert gas at a pressure of say 6 psi.

In a typical operating sequence, the nozzle 6 is removed from the rinse station 22 and is then positioned over the beaker 8 containing the blank solution. At that stage, the nozzle 6 and capilliary tube 10 are preferably full of the rinse solution 28 save for a slug of air 32 (FIG. 2)—e.g., 10 l at the very tip of the nozzle 6. The nozzle 6 is lowered into the beaker 8 located at the station 21 and which in the example under consideration contains a blank solution. The syringe 11 is then operated to draw up a predetermined quantity of that solution and a corresponding quantity of rinse solution 28 is of course displaced out of the nozzle 6 in the process. The nozzle 6 is then lifted out of the blank solution beaker 8 and the syringe 11 is again actuated to draw in another 10 l slug (for example) of air 12. That operation is then repeated for each other ingredient or solution required to be transferred to the tube furnace 5 for the particular analysis step.

By way of example, the final contents of the capilliary tube 10 and nozzle 6 may be a quantity of rinse solution 28, slug of air 32, blank solution 1, slug of air 12, matrix modifier 2, slug of air 12, standard solution 3, slug of air 12, sample solution 4 and slug of air 33, arranged in that order with the rinse solution 28 remote from the tip of the nozzle 6 (FIG. 1). As the blank solution and matrix modifier are contained in respective beakers 8, the turntable 14 needs to be rotated by associated stepper motor 34 during the course of the pick-up operation to place each of those beakers 8 in turn at the station 21.

It may be desirable to clean the exterior of the nozzle 6 between successive solution take-up operations so as to minimise or avoid cross-contamination of the solutions. By way of example, the nozzle 6 may be dipped into a body of rinse solution 28 immediately following the up-take of each slug of air 12. The nozzle 6 may then be transferred to the location at which the next ingredient or solution is to be taken up. In the arrangement shown, the body of rinse solution 28 is contained in an open-topped rinse chamber 35 located at the rinse station 22.

After all solutions have been taken up by the nozzle 6, it is moved to the deposition station 23 at which it is lowered to locate within or over the access opening 9 formed through a wall of the tube furnace 5. The syringe 11 is then operated to expell the sample, standard, matrix modifier and blank solutions 4, 3, 2 and 1 respectively, together with say one half of the air slug 32 immediately adjacent the rinse solution 28. Each expelled solution separately approaches the internal surface 36 (FIGS. 1 and 2) of the furnace 5 although in rapid succession and mixing of the solutions occurs at or adjacent to that surface 36. The mix ingredients are therefore transported and deposited in an efficient manner and under accurate quantity control.

After deposition at the furnace 5, the nozzle 6 is returned to the rinse station 22 at which a quantity of rinse solution 28 is passed through the capilliary tube 10 from the rinse solution container 29 and is ejected through the nozzle 6. The ejection may take place while the nozzle is located in the body of rinse solution 28 contained in the rinse chamber 35 and an overflow 37 for that chamber 35 may allow escape of excess solution. When the ejection operation is completed, it is preferred that the nozzle 6 be left dipped within the body of rinse solution 28 until required for another sequence of operations. The commencement of the next sequence involves withdrawl of the nozzle 6 from the rinse chamber 35 and subsequent actuation of the syringe 11 to draw in a 10 l slug of air 32 at which time the pick-up device is ready to be moved into position for up-take of the blank solution (for example).

In the particular sequence described, the aliquots of sample and standard solutions 4 and 3 respectively (FIG. 1) are the first and second respectively in order of deposition in the furnace 5 and consequently those solutions are fully purged from the nozzle 6.

In the apparatus described it is preferred to provide a limit stop (not shown) at or adjacent the deposition station 23 so as to accurately determine the lowered position of the nozzle 6 at that station. The furnace 5 need not be at full operating temperature at the time of deposition of the sample mixture. At that ime, the furnace 5 may be cooled or heated only to a relatively low temperature. Furthermore, although the various ingredients are described as separately approaching the furnace internal surface 36, there may be circumstances under which the ingredients coalesce at the tip of the nozzle 6 before leaving that tip to approach the surface 36 as a single droplet. The intervening air slugs 12 perculate or diffuse through the droplet under those circumstances.

Still further, it is not necessary to have the nozzle 6 separate from the conduit 10. Indeed, it is generally preferred that an end portion of the conduit 10 forms the nozzle 6.

The method and apparatus described provides a substantial improvement over the prior methods and apparatus used for sample handling. The method enables convenient selection of sample ingredients in terms of nature and/or quantity. It enables convenient addition of known standards to unknown samples for the purpose of standard addition methods and also enables addition of chemical matrix modifiers in an atomic fashion, which is a substantial improvement over the prior manual method. Automatic control avoids operator error and contamination of solutions and the time required for a particular analysis procedure is substantially reduced. Mixture of the ingredients within the furnace tube immediately prior to analysis has several advantages including minimising losses through absorption and precipitation.

It is to be understood that various alterations, modifications and/or additions may be introduced into the constructions and arrangements of parts previously described without departing from the spirit or ambit of the invention as defined by the appended claims.

Having now described out invention what we claim as new and desire to secure by Letters Patent is:

1. A sample handling method including the steps of, loading into a conduit in sequence a quantity of one ingredient of a solution mixture, a slug of separating fluid and a quantity of another ingredient of said mixture, and depositing said ingredients in last-in, first-out succession at a deposition zone in a single operation, the final ingredient loaded and first deposited being an ingredient of unknown compositional characteristics.

2. Sample handling apparatus including, a conduit, a nozzle at one end of said conduit, a plurality of pick-up stations at which respective components of a segmented fluid stream to be carried by said conduit are located, a furnace operable to atomize a liquid sample deposited therein, said pick-up stations comprising at least one blank solution station, at least one standard solution station, and at least one sample solution station, support means carrying said nozzle and being operable to locate said nozzle in a selected sequence at each of said stations and subsequently at said furnace, loading means operable to cause a said component to be loaded into said conduit when said nozzle is at the respective said station and also being operable to load a slug of separating fluid into said conduit between each two adjacent said components, control means for establishing and effectuating said selected sequence locating said support means in turn at different said pick-up stations, said sequence terminating at said sample solution pick-up station, and a discharge means operable to discharge at least part of said fluid stream from said conduit when said nozzle is located at said furnace.

3. Apparatus to claim 2, wherein said loading means includes a source of negative pressure and said discharge means includes a source of positive pressure, both said sources being connected to said conduit at a location remote from said nozzle.

4. Apparatus according to claim 3, wherein a syringe provides both said sources and a stepper motor is connected to the plunger of said syringe to move that plunger in either of two directions according to whether the syringe is to be used in the loading mode or the discharge mode.

5. Apparatus according to claim 4, wherein a source of rinsing fluid is connected to said conduit at a location between said syringe and said nozzle, and a valve controls communication between said rinsing fluid source and said conduit.

6. Apparatus according to claim 2, including a rotatable table operable to support a plurality of containers for holding respective said components and being movable to position a selected said container at a selected said station.

7. Apparatus according to claim 6, wherein said support means includes an arm to which said nozzle is connected, a pivotal mounting of said arm by which said nozzle is movable through an arcuate path which passes through said table and at least reaches said furnace, and means for lowering and raising said arm to move said nozzle into and out of respectively a said container.

8. Apparatus according to claim 7, wherein a rinse solution bath is located in said arcuate path and said lowering and raising means is operable to move said nozzle into and out of said bath.

9. Sample handling apparatus including, a conduit, a nozzle at one end of said conduit, sources of positive and negative pressure connectable to said conduit at a location remote from said nozzle, a plurality of pick-up stations at which respective components of a segmented fluid stream to be carried by said conduit are located, support means carrying said nozzle and being movable to locate said nozzle in a selected sequence at each of said stations and subsequently at a deposition zone, the terminal said station of said selected sequence comprising said sample substance, and control means for establishing and effectuating said selected sequence of nozzle locations.

* * * * *